(12) United States Patent  
Phelps

(10) Patent No.: US 9,128,011 B1
(45) Date of Patent: Sep. 8, 2015

(54) METHOD AND DEVICE FOR TESTING EXTRACTION LOAD

(71) Applicant: ASSOCIATE PROFESSIONAL ENGINEERING & CONSTRUCTION LLC, Galveston, TX (US)

(72) Inventor: Matthew Bernard Phelps, Galveston, TX (US)

(73) Assignee: ASSOCIATE PROFESSIONAL ENGINEERING & CONSTRUCTION LLC, Galveston, TX (US)

( * ) Notice: Subject to any disclaimer, the term of this patent is extended or adjusted under 35 U.S.C. 154(b) by 0 days.

(21) Appl. No.: 14/139,702

(22) Filed: Dec. 23, 2013

Related U.S. Application Data

(63) Continuation-in-part of application No. 12/931,772, filed on Feb. 10, 2011, now abandoned.

(60) Provisional application No. 61/303,535, filed on Feb. 11, 2010.

(51) Int. Cl.
    *G01N 3/00* (2006.01)
    *G01N 3/08* (2006.01)
    *G01N 3/02* (2006.01)

(52) U.S. Cl.
    CPC .................................... *G01N 3/02* (2013.01)

(58) Field of Classification Search
    USPC .................................................. 73/788
    See application file for complete search history.

(56) References Cited

U.S. PATENT DOCUMENTS

| 4,632,220 A | 12/1986 | Murrell |
| 4,916,955 A | 4/1990 | Katsuoka et al. |
| 5,212,654 A | 5/1993 | Deuar |
| 6,494,103 B1 * | 12/2002 | Loong ............................ 73/788 |
| 6,758,019 B2 | 7/2004 | Kalkanoglu et al. |
| 6,935,196 B1 | 8/2005 | Tumlin |
| 7,155,987 B1 * | 1/2007 | Tumlin ..................... 73/862.393 |
| 2004/0112353 A1 * | 6/2004 | Stewart et al. ................ 124/20.1 |
| 2009/0235718 A1 * | 9/2009 | Fox .............................. 73/12.06 |

* cited by examiner

*Primary Examiner* — Lisa Caputo
*Assistant Examiner* — Jamel Williams
(74) *Attorney, Agent, or Firm* — Buskop Law Group, PC; Wendy Buskop

(57) ABSTRACT

A method and device for objectively determining extraction loads for, or verifying capability to withstand loads for fasteners, sealants, or overlying materials attached to an underlying material. The method provides for a repeatable and objective test for comparing extraction load and load bearing capability of fasteners, sealants, or overlying materials attached to an underlying material to standards for the same. The portable device provides for testing various types of fasteners, sealants, or overlying materials attached to an underlying material in a repeatable and easily usable manner. The device comprises a means of generating, applying, and measuring load forces, and providing the data therefrom.

18 Claims, 7 Drawing Sheets

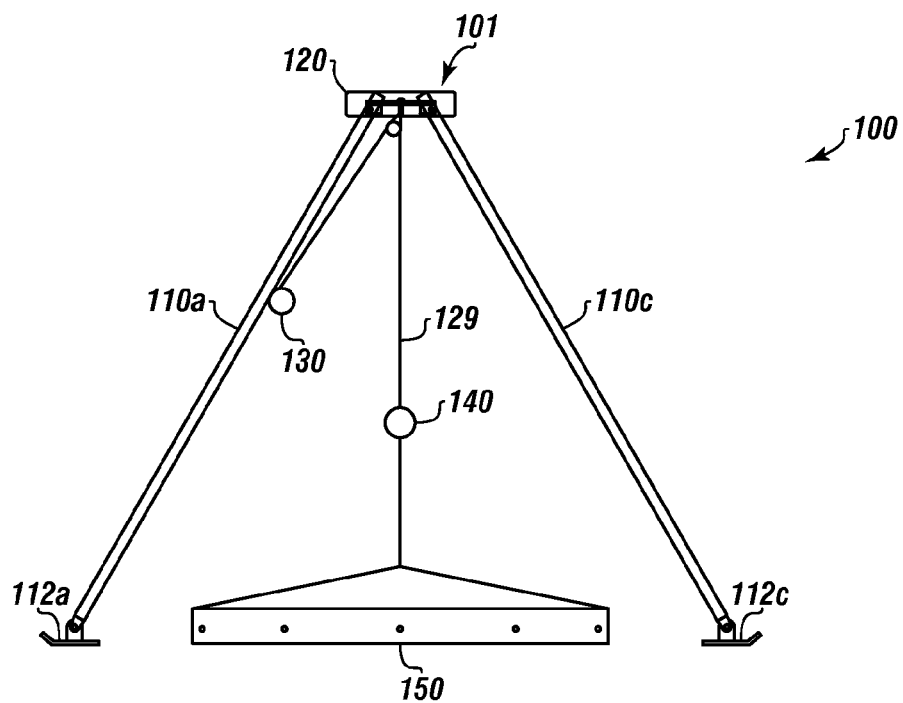
FIGURE 1
FIGURE 2
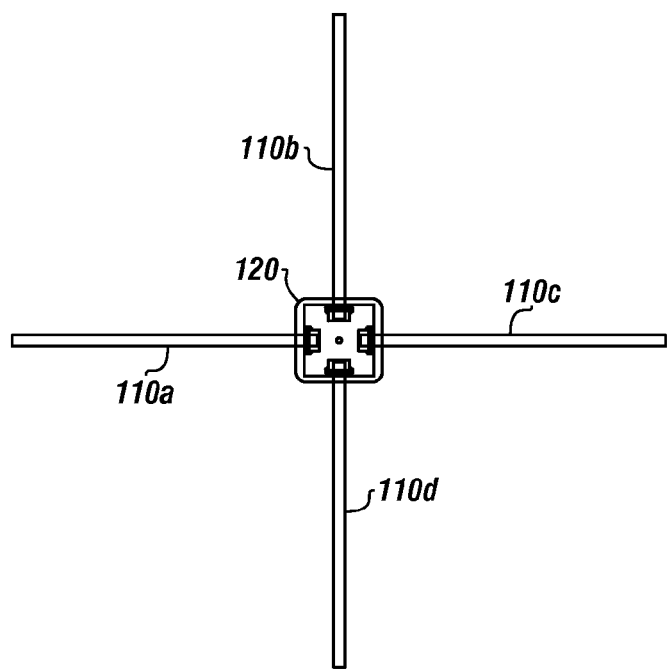

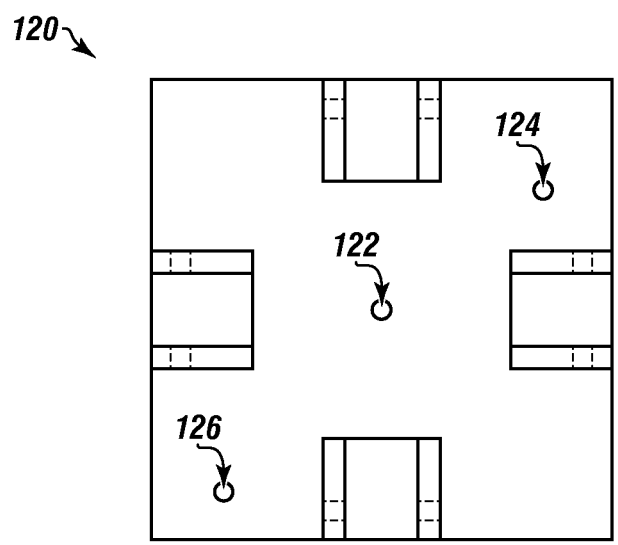
FIGURE 5A
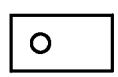    
FIGURE 5B    FIGURE 5C

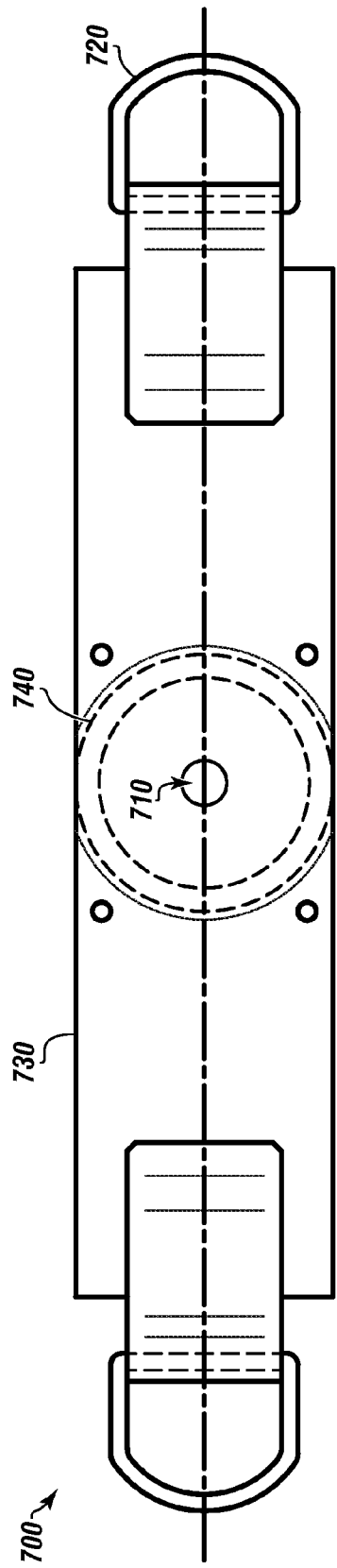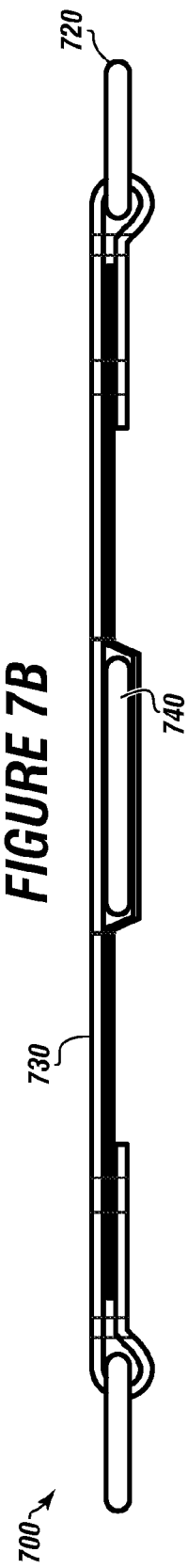
FIGURE 7A
FIGURE 7B

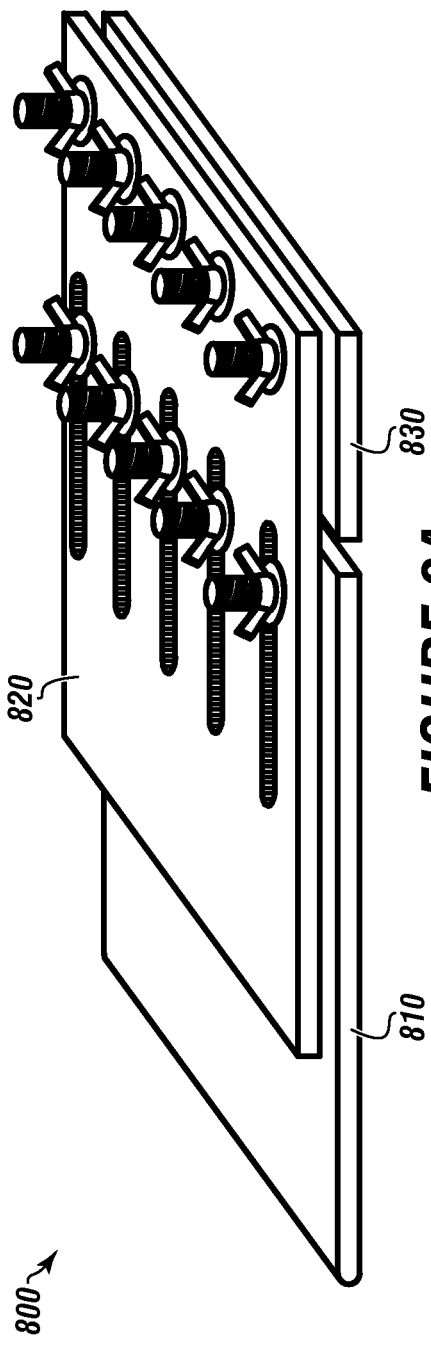
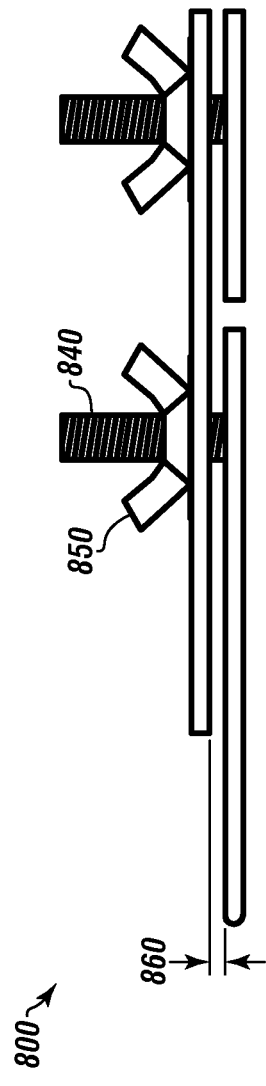
FIGURE 8A
FIGURE 8B

METHOD AND DEVICE FOR TESTING EXTRACTION LOAD

CROSS REFERENCE TO RELATED APPLICATIONS

The current application is a Continuation in Part and claims the benefit of co-pending U.S. patent application Ser. No. 12/931,772 filed on Feb. 10, 2011, entitled "IN SITU ROOF COVERING TEST METHOD & DEVICE," which claims priority to U.S. Provisional Patent Application Ser. No. 61/303,535 filed on Feb. 11, 2010 entitled, "IN SITU ROOF COVERING TEST METHOD & DEVICE." These references are hereby incorporated in their entirety.

FIELD

The present embodiments generally relate to the field of forensic engineering investigation, testing, and reporting and more specifically to a method and device for in situ testing of the strength of coverings, sealants, and fasteners. One particularly useful application is the testing of shingles as well as the strength of a roof covering sealant and fastening system. The in situ extraction load test method and device is capable of measuring and comparing actual sealant strength, actual fastener strength, or a combination of both to calculated, expected, required, or other values.

BACKGROUND

A need exists for an objective, in situ method for objectively determining fastener strength and the attachment strength of fastened items.

Often, methods of determining damage to fasteners sealants, coverings, attached materials, and the like is subjective and imprecise. For example, storm damage assessments for shingles on roofs are accomplished by pulling on shingles to subjectively determine attachment strength.

A further need exists for a versatile and portable device capable of testing multiple types of fasteners, sealants, coverings, and the like, as well as their attachment strength.

The present embodiments meet these needs by providing an easily portable device and method capable of testing and comparing the force required to extract a fastener or an overlying material from an underlying material. Further, the invention allows for the collection, recordation, and comparison of data in a verifiable and consistently repeatable manner.

Safety, efficiency, and cost savings will be affected through implementation of the present invention.

Structures and objects in need of repair can be objectively identified and failures prevented through the use of preventive maintenance. Proper scheduling of maintenance and repairs, avoidance of unnecessary maintenance and repairs, and identification of need for maintenance and repairs can all be drastically improved through implementation of the present invention.

This can translate to a safe operating environment for personnel, avoidance of costly failures, or unnecessary cost for needless procedures in a variety of settings industrially, commercially, residentially, and the like.

BRIEF DESCRIPTION OF THE DRAWINGS

The detailed description will be better understood in conjunction with the accompanying drawings as follows:

FIG. 1 depicts a side view of one embodiment of the device for measuring extraction load.

FIG. 2 depicts a top view of one embodiment of the device for measuring extraction load.

FIGS. 5A-5C depict a top view of a top plate of one embodiment of the device for measuring extraction load.

FIGS. 7A and 7B depict an attachment usable with one embodiment of the device for measuring extraction load.

FIGS. 8A and 8B depict an attachment usable with one embodiment of the device for measuring extraction load.

Figure 3A:
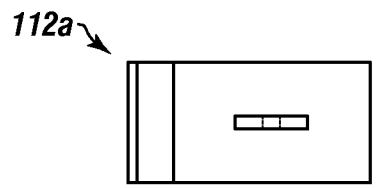
FIGS. 3A-3C depict a detail view of a foot of one embodiment of the device for measuring extraction load.

The present embodiments are detailed below with reference to the listed Figures.

DETAILED DESCRIPTION OF THE EMBODIMENTS

Before explaining the present apparatus and methods in detail, it is to be understood that the apparatus and methods are not limited to the particular exemplary embodiments and that it can be practiced or carried out in various ways.

Specific structural and functional details disclosed herein are not to be interpreted as limiting, but merely as a basis of the claims and as a representative basis for teaching persons having ordinary skill in the art to variously employ the present invention.

The present embodiments relate to a device and method for measuring the extraction load of a fastener or an overlying material to determine the integrity of the attachment. The method can indicate damage, wear, or other degradation of the fastener, sealant, overlying material or underlying material.

Such forensic data is widely pertinent to many industrial, manufacturing, fabrication, commercial construction, residential construction, and other applications. However, as testing the attachment strength of shingles on a roof is one particularly instructive example of applying both the device and the method disclosed herein. Many examples will refer to such an application.

In the forensic engineering industry, roof damage assessments are based upon physical inspection and estimation of the number of damages areas per 100 ft$^2$ of roof area. If the number of damages areas exceeds the acceptable limit, then the roof covering is considered to have failed and should be replaced.

Roof coverings (and in particular shingles) that are lifted by the force of wind during storms can result in separation of the sealant located on the bottom of the roof covering as well as failure of the fasteners holding the roof covering in place.

While both the sealant and the fasteners are designed to hold the roof covering in place. The sealant, when properly applied and positioned, further provides waterproofing for the roof system. In fact, building codes require certificates demonstrating that a roof covering installed on a structure is certified to withstand predetermined wind loads.

The American Society for Testing and Materials (ASTM), American Society of Civil Engineers (ASCE), and American National Standards Institute/Underwriters Laboratories (ANSI/UL) provide a variety of test methods by which a roof covering system can be certified based upon successful laboratory testing.

Some of the ASTM test methods and supporting documentation includes: ASTM D1079 Terminology Relating to Roofing and Waterproofing, ASCE7-02 Minimum Design Loads for Buildings and Other Structures, ASTM D7158-08d Standard Test Method for Wind Resistance of Asphalt Shingles, ASTM D225 Specification for Asphalt Shingles (Organic Felt) Surfaced with Mineral Granules, ASTM D3161 Test Method for Wind-Resistance of Asphalt Shingles (Fan-Induced Method), and ASTM D6381 Test Method for Measurement of Asphalt Shingle Mechanic Uplift Resistance.

ANSI/UL laboratory test methods include ANSI/UL2390-04 Test Method for Wind Resistant Asphalt Shingles with Sealed Tabs.

These tests and certification methods are limited to the laboratory environment and are intended for testing new undamaged roof coverings. A roof covering that is lifted by the force of the wind such that the sealant separates, but the fastener continues to hold is considered to be "wind lifted."

Some forensic engineers do not consider "wind lifted" roof coverings as damage based on the notion that the sealant will reseal with time and perform as previously rated. This notion is supported by the forensic engineer's subjective test of tugging on the roof covering to determine the resistance of the sealant to separate.

Such a subjective test lacks objective measurement(s), documentation, and repeatability. The present invention improves the present methodology by providing a new, novel, and repeatable test method and device to measure, in situ, the strength of an installed roof covering system and further compare the measured values against relevant predetermined values to determine if the roof covering system is damaged and whether replacement is required.

Such methodology is easily analogized and ported to testing storm damaged, weathered, aging, or otherwise damaged components such as cabling attached to wooden and concrete structures with bolts or rivets, items fastened with nails and tacks, or items glued together.

Testing can provide data on the integrity of the fastener or sealant or the integrity of the underlying material to "hold" the fastener or sealant. For example, rotting wood may not have the same capability to robustly hold a nail driven into it, or concrete that has been pitted and eroded may not have the same capability to robustly hold a bolt driven into it.

This information can be particularly useful to determine requirements for and the timing of maintenance, repairs, or replacement of underlying materials, fasteners, coverings, sealants, attached structures, or the like, and any combination thereof.

The novel method eliminates subjectivity of fastener, sealant, and covering strength determinations through application of widely established and accepted standards for performance and safety to these determinations. The method provides for repeatable, objective, documentable, and consistent testing in situ.

The method involves creating and maintaining a database, wherein the database comprises extraction load values of various fasteners or overlying materials, deployed on or in various underlying materials and also comprises established standards.

Overlying materials refer to coverings or other objects attached with a fastener, a sealant, or any other fastening means to an underlying material. Applying load to an overlying material provides a means for determining the sealant or fastener strength attaching the overlying material to an underlying material.

For example, in the instance of determining storm damage to roofs, the database can include required sealant strength for shingles on a roof with wooden decking. It can further comprise required fastener strength for wooden decking on a roof with wooden rafters.

While a single database can be convenient to the user of this method and device, multiple separate databases in communication together can serve to perform the function of a single database as disclosed herein. Further, database as used herein can refer to charts, spreadsheets, tables, and the like used to store and present information, whether accessed with the aid of a computer or manually by a user.

The method can further comprise deploying a device for measuring extraction load. While the device itself will be discussed in much greater detail below, the device preferably is portable, usable in situ, and can transmit data for the purposes of analysis, documentation, supporting evidence, and the like.

The method can further comprise applying an extraction load to a fastener or overlying material which is connected to an underlying material sufficient to extract the fastener or overlying material from the underlying material. In the alternative, a predetermined load can be applied to verify that the fastener or overlying material can withstand this load without detaching from the underlying material.

The predetermined load can be based upon established and accepted standards to verify integrity of items such as roof coverings or simply selected by the user.

The method can further comprise measuring a load required to extract a fastener or overlying material from an underlying material. In the alternative, the method can comprise verifying that the fastener or overlying material withstood the predetermined load without detaching. The discussion of the device below will provide further narrative with respect to accomplishing this step.

The method can further comprise comparing the load required to extract the fastener from the underlying material to the extraction load values and established standards in the database. The standards are preferably widely accepted and established, such as those published by ASTM, ANSI/UL, ASCE, and the like. However, standards can be established by the user based upon empirical data, theory, historical information, predicted values, and the like.

The method, therefore, eliminates subjectivity and variability in testing attachment strengths such as those for roof coverings. Compiling, storing, and analyzing data will provide much more germane criteria for maintenance, repair, and replacement decisions.

Various methods both computer and human implemented can be used for compiling, storing, and analyzing the data acquired.

For example, a computer program can be stored on a non-transitive medium with instructions comprising storing acquired values within a spreadsheet or database, and displaying data relevant to measured values, standards, and recommended decisions based upon the application of this method.

Various implementation steps of this method can be controlled by such a program with a graphical or textual user interface by persons having ordinary skill in the art to implement this method.

The method can also be manually implemented utilizing charts containing established standards and extraction load data acquired in situ.

The device for implementing this method is ideally portable, lightweight, adjustable for placement at various orientations, easily adaptable to various fastener and overlying material types, and capable of generating a wide range of load forces at various orientations.

The device can comprise a base adapted to be supported by an underlying material. The base comprises a device platform and a plurality of legs. The device platform need not be a flat plate as is traditionally envisioned. The device platform can be as simple as a hinged attachment connecting the plurality of legs, or a plate providing a surface upon which devices can rest, as in the embodiment shown in the figures as discussed below.

In some embodiments, the device platform can support an extraction load generator, or can provide a work surface upon which a user can rest tools, a laptop, etc.

The plurality of legs can allow the base to be supported by the underlying material. For example, in some embodiments the legs can rest upon surrounding shingles of a shingle to be tested and be supported by the underlying structure of a roof.

Material selection of the legs can be dependent upon the application. Lightweight plastics, wood, metals, or hybrid materials can be selected based upon the desired load bearing characteristics required by persons having ordinary skill in the art.

The legs can be adjustable in length, such as by incorporating a telescopic design. The legs can also incorporate various folding and hinged sections, slidable and lockable segments, or the like for length adjustment. It will be obvious to persons having ordinary skill in the art that adjustable legs will allow for testing of fasteners and overlying materials by applying forces from a multitude of angles. For example, a shingle need not be extracted perpendicularly away from roof decking, but can be extracted at an angle of the user's choosing.

The number of legs can be variable based upon the application. For example, for ease of portability and minimizing weight, a three leg or a four leg embodiment can be utilized for testing roof coverings.

However, embodiments can incorporate a multitude of legs for greater load bearing capability, for more even distribution of load to the underlying material, for fine adjustments to the orientation of the device, or to support a larger device platform, thereby allowing for multiple tests encompassing a large surface area.

Each of the legs can incorporate a foot to rest securely on and be securely supported by an underlying material. The foot can be rubberized, or otherwise comprise non-slip materials or coatings. The foot can further contain a facility for attachment to vertical or angled underlying material, such as a bolt or screw hole or tacky or adhesive substance coating the underside.

The device can further comprise an extraction load generator. The extraction load generator can generate the load or force applied to a fastener or overlying material. Some examples of an extraction load generator are: a winch, a spring, a pulley, a motor, and the like, or combinations thereof.

The device further comprises an extraction load applicator for applying the load or force to a fastener or overlying material. The extraction load applicator can be a rope, a chain, a rod, a screw, or any applicable means of transmitting the force or load generated by the extraction load generator.

The extraction load applicator can be made positionally adjustable with respect to the device platform to allow for multiple tests without relocating the device.

The extraction load applicator can have a plurality of interchangeable attachments for connection to various types of fasteners and overlying materials. Examples of attachments are in FIGS. 6, 7, and 8. Further attachments specific to an application of the device can be used.

The device can further comprise a means for measuring the load generated by the extraction load generator. Depending on the type of extraction load generator implemented, various means of measuring the load generated by the extraction load generator can be utilized. Some examples of a means for measuring the load generated by the extraction load generator are: an electrical current meter, a scale, a measurement of the number of turns on a winch, a hydraulic load cell, a pneumatic load cell, a piezoelectric load cell, a strain gauge, and the like, or combinations thereof.

The means for measuring the load generated by the extraction load generator can also comprise a means to transmit a measured load generated to an electronic device. The electronic device can be a simple display of a value of the measured load, or a computing device capable of storing the data for a period of time.

Turning now to the Figures, FIG. 1 depicts a side view and FIG. 2 depicts a top view of an embodiment of the device for measuring extraction load 100.

In this embodiment, the device for measuring extraction load 100 comprises a base 101 which comprises a device platform 120 and a plurality of legs 110a-110d attached to the device platform 120. The plurality of legs 110a-110d each comprise feet 112a-112d for the device for measuring extraction load 100 to be supported by an underlying material.

An extraction load generator 130 is shown in contact with an extraction load applicator 129. For example, an embodiment can employ a winch as the extraction load generator 130 in combination with a rope as the extraction load applicator 129.

The means for measuring the load generated by the extraction load generator 140 is shown in this embodiment as disposed between the device platform 120 and the interchangeable attachment 150. For example, one embodiment can employ a load cell as the means for measuring the load generated by the extraction load generator 140.

It is to be noted that, while this is one disposition of the elements required, numerous combinations of placements exist for these elements. The size and shape of the device platform 120 can offer much flexibility in the exact location of the elements.

Figure 3B:
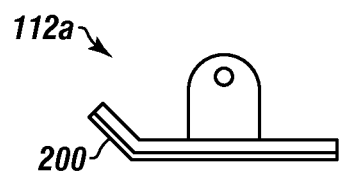
Figure 3C:
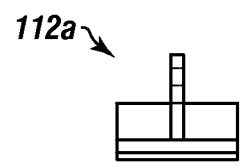
Figure 4A:
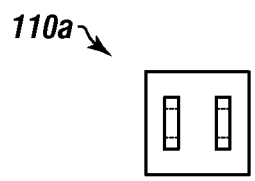
FIGS. 4A-4C depict a detailed view of a bottom of a leg of one embodiment of the device for measuring extraction load.
Figure 4B:
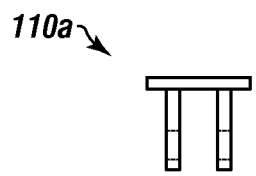
Figure 4C:
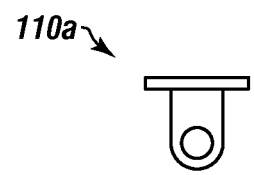

FIGS. 3A-3C depict a detail view of a foot 112a of an embodiment of the device for measuring extraction load. The foot 112a can be fastened to the leg 110a utilizing connector at the bottom of a leg 110a such as the one depicted in FIGS. 4A-4C.

FIGS. 5A-5C depict a top view of a device platform 120 of one embodiment of the device for measuring extraction load. This device platform 120 embodiment allows for the placement of an extraction load generator 140 atop it, and shows a centrally located hole 122 through which an extraction load applicator 129 can be passed, however, alternate holes 124 and 126 can be contemplated for allowing multiple tests without relocating the device for measuring extraction load 100.

Figure 6A:
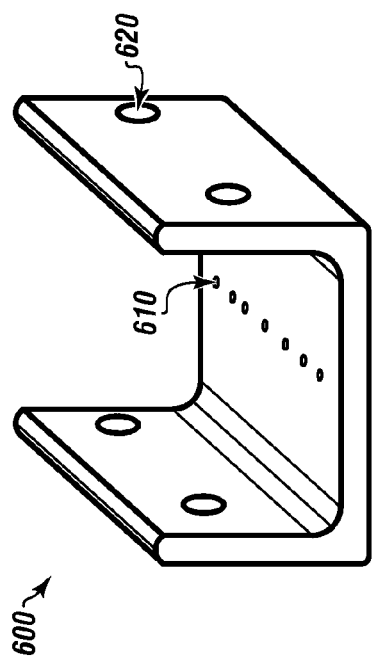
FIGS. 6A and 6B depict an attachment usable with one embodiment of the device for measuring extraction load.
Figure 6B:
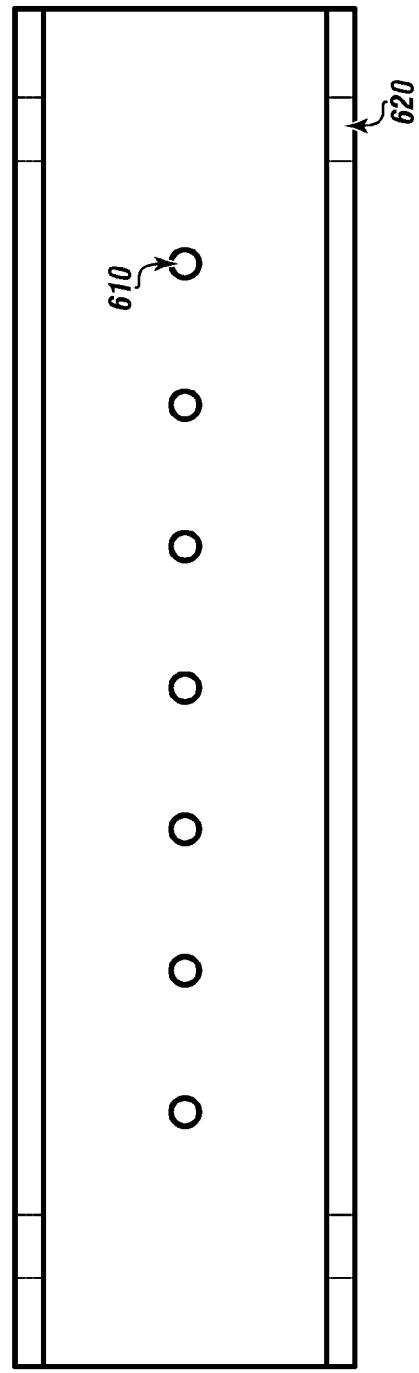

FIGS. 6A and 6B depict an attachment usable with one embodiment of the device for measuring extraction load. Attachment holes 620 for attachment to the extraction load applicator 129, and testing hole 610 is shown. For example, this embodiment can be used to test the strength of a nail in a rafter, by driving a nail through testing hole 610 in to a rafter, and performing the disclosed method.

FIGS. 7A and 7B depict an attachment usable with one embodiment of the device for measuring extraction load. Attachment ring 720 for attachment to the extraction load applicator 129, and testing hole 710 is shown. A strap 730 with a reinforcing ring 740 incorporated is shown. For example, this embodiment can be used to test the strength of a bolt driven into concrete through testing hole 710, and performing the disclosed method.

FIGS. 8A and 8B depict an attachment usable with one embodiment of the device for measuring extraction load. Plates 810, 820 and 830 are shown attached together utilizing a bolt 840 and a nut 850. This embodiment allows for a user to adjust the space 860 between plate 810 and plate 820. Attachment to the extraction load applicator 129 can be made by treading the bolt 840 into the extraction load applicator 129. For example, this embodiment can be used to test the strength of a shingle, by sliding the attachment on to a shingle such that the shingle is located in the space 860 in between plate 810 and plate 820, and performing the disclosed method.

Figure 9:
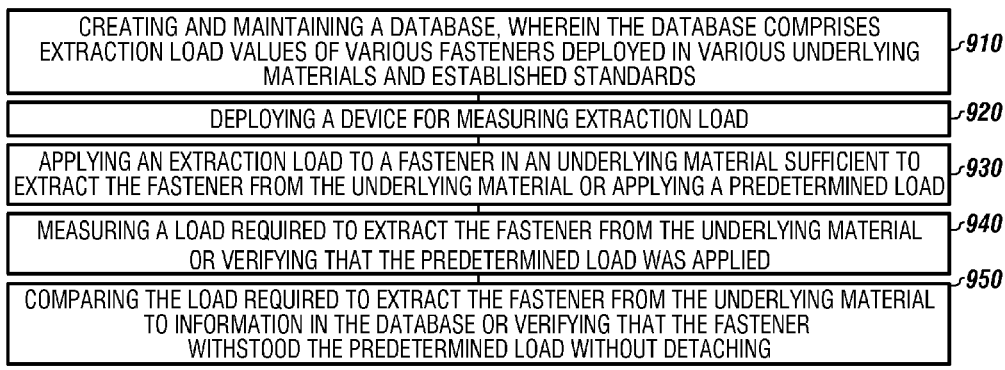
FIG. 9 depicts the steps for a method of measuring extraction load values of fasteners.

FIG. 9 depicts the steps for an embodiment of the method of measuring extraction load values of fasteners.

The method can include creating and maintaining a database, wherein the database comprises extraction load values of various fasteners deployed in various underlying materials and established standards, as shown in step 910.

The method can include deploying a device for measuring extraction load, as shown in step 920.

The method can include applying an extraction load to a fastener in an underlying material sufficient to extract the fastener from the underlying material or applying a predetermined load, as shown in step 930.

The method can include measuring a load required to extract the fastener from the underlying material or verifying that the predetermined load was applied, as shown in step 940.

The method can include comparing the load required to extract the fastener from the underlying material to information in the database or verifying that the fastener withstood the predetermined load without detaching, as shown in step 950.

Figure 10:
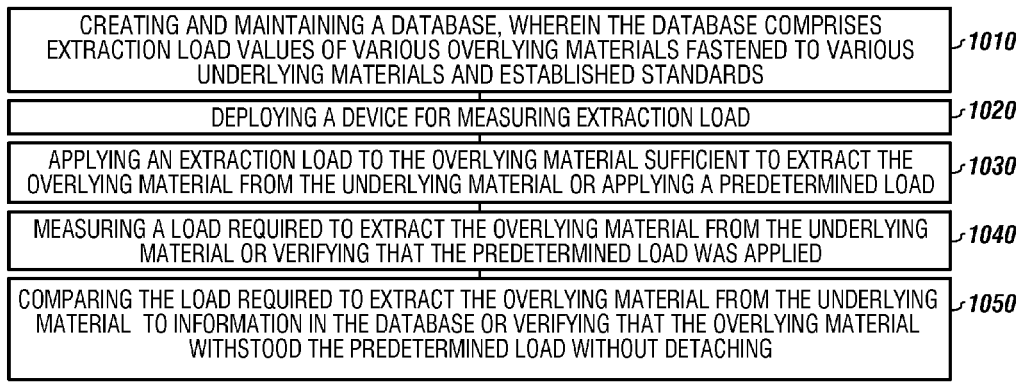
FIG. 10 depicts the steps for a method of measuring extraction load values of overlying materials.

FIG. 10 depicts the steps for an embodiment of a method of measuring extraction load values of overlying materials.

The method can include creating and maintaining a database, wherein the database comprises extraction load values of various overlying materials fastened to various underlying materials and established standards, as shown in step 1010.

The method can include deploying a device for measuring extraction load, as shown in step 1020.

The method can include applying an extraction load to the overlying material sufficient to extract the overlying material from the underlying material or applying a predetermined load, as shown in step 1030.

The method can include measuring a load required to extract the overlying material from the underlying material or verifying that the predetermined load was applied, as shown in step 1040.

The method can include comparing the load required to extract the overlying material from the underlying material to information in the database or verifying that the overlying material withstood the predetermined load without detaching, as shown in step 1050.

While these embodiments have been described with emphasis on the embodiments, it should be understood that within the scope of the appended claims, the embodiments might be practiced other than as specifically described herein.

What is claimed is:

1. A device for measuring an extraction load comprising:
    a. a base adapted to be supported by an underlying material, wherein the base comprises:
        (i) a device platform; and
        (ii) a plurality of legs attached to the device platform; and
        wherein the base provides a stable foundation to test a fastener or an overlying material attached to the underlying material;
    b. an extraction load generator supported by the base;
    c. an extraction load applicator in contact with the extraction load generator, wherein the extraction load applicator transmits a load generated by the extraction load generator to the fastener or the overlying material, and wherein the extraction load applicator comprises a plurality of interchangeable attachments for connecting to different types of fasteners or for connecting to different types of overlaying materials; and
    d. a means for measuring the load generated by the extraction load generator.

2. The device of claim 1, wherein the device platform is a plate.

3. The device of claim 1, wherein the plurality of legs are independently adjustable in length to orient the device platform at a desired angle.

4. The device of claim 1, wherein the extraction load generator is:
    a. a winch;
    b. a spring;
    c. a pulley;
    d. a motor; or
    e. combinations thereof.

5. The device of claim 1, wherein the means for measuring the load generated by the extraction load generator is:
    a. an electrical current meter;
    b. a scale;
    c. a measurement of the number of turns on a winch;
    d. a hydraulic load cell;
    e. a pneumatic load cell;
    f. a piezoelectric load cell;
    g. a strain gauge; or
    h. combinations thereof.

6. The device of claim 1, wherein the means for measuring the load generated by the extraction load generator comprises a means to transmit a measured load generated to an electronic device.

7. The device of claim 1, wherein the extraction load applicator is positionally adjusted relative to the device platform.

8. The device of claim 1, wherein each of the plurality of legs comprises a means for attachment to angled or vertical surfaces.

9. A method for measuring an extraction load comprising:
    a. creating and maintaining a database, wherein the database comprises extraction load values of various fasteners deployed in various underlying materials and established standards;
    b. deploying a device for measuring extraction load;
    c. applying the extraction load to a fastener in an underlying material sufficient to extract the fastener from the underlying material or applying a predetermined load;
    d. measuring a load required to extract the fastener from the underlying material or verifying that the predetermined load was applied; and e. comparing the load required to extract the fastener from the underlying material to information in the database or verifying that the fastener withstood the predetermined load without detaching.

10. The method of claim 9, further comprising determining an integrity of a coupling between the fastener and the underlying material.

11. The method of claim 9, further comprising storing data from a test.

12. The method of claim 9, wherein the established standards pertain to:
   a. material composition of fasteners;
   b. material composition of the underlying material;
   c. construction guidelines and specifications;
   d. safety; or
   e. combinations thereof.

13. The method of claim 10, further comprising comparing the integrity of the coupling between the fastener and the underlying material to an established standard.

14. A method for measuring an extraction load comprising:
   a. creating and maintaining a database, wherein the database comprises extraction load values of various overlying materials fastened to various underlying materials and established standards;
   b. deploying a device for measuring extraction load;
   c. applying the extraction load to the overlying material sufficient to extract the overlying material from the underlying material or applying a predetermined load;
   d. measuring a load required to extract the overlying material from the underlying material or verifying that the predetermined load was applied; and
   e. comparing the load required to extract the overlying material from the underlying material to information in the database or verifying that the overlying material withstood the predetermined load without detaching.

15. The method of claim 14, further comprising determining an integrity of a coupling between the overlying material and the underlying material.

16. The method of claim 14, further comprising storing data from a test.

17. The method of claim 14, wherein the established standards pertain to:
   a. material composition of overlying materials;
   b. material composition of the underlying material;
   c. construction guidelines and specifications;
   d. safety; or
   e. combinations thereof.

18. The method of claim 15, further comprising comparing the integrity of the coupling between the overlying material and the underlying material to an established standard.

* * * * *